(12) United States Patent
Cosmescu (10) Patent No.: US 11,259,863 B2
(45) Date of Patent: Mar. 1, 2022

(54) MONOPOLAR ELECTROSURGERY BLADE AND ELECTROSURGERY BLADE ASSEMBLY

(71) Applicant: I.C. Medical, Inc., Phoenix, AZ (US)

(72) Inventor: Ioan Cosmescu, Phoenix, AZ (US)

(73) Assignee: L.C. Medical, Inc., Phoenix, AZ (US)

( * ) Notice: Subject to any disclaimer, the term of this patent is extended or adjusted under 35 U.S.C. 154(b) by 499 days.

(21) Appl. No.: 15/912,855

(22) Filed: Mar. 6, 2018

(65) Prior Publication Data

US 2018/0256244 A1 Sep. 13, 2018

Related U.S. Application Data

(60) Provisional application No. 62/467,558, filed on Mar. 6, 2017, provisional application No. 62/576,207, filed on Oct. 24, 2017.

(51) Int. Cl.
*A61B 18/14* (2006.01)
*A61B 18/00* (2006.01)

(52) U.S. Cl.
CPC ............ *A61B 18/1402* (2013.01); *A61B 2018/00077* (2013.01); *A61B 2018/00083* (2013.01); *A61B 2018/00107* (2013.01); *A61B 2018/00589* (2013.01); *A61B 2018/00601* (2013.01); *A61B 2018/1412* (2013.01)

(58) Field of Classification Search
CPC ...... A61B 18/1402; A61B 2018/00589; A61B 2018/00601; A61B 2018/1412; A61B 2018/00077; A61B 2018/00083; A61B 2018/00107

USPC .......................................................... 606/45
See application file for complete search history.

(56) References Cited

U.S. PATENT DOCUMENTS

| | | | |
|---|---|---|---|
| 4,770,067 A | | 9/1988 | Liu et al. |
| 5,125,927 A | * | 6/1992 | Belanger ............ A61B 18/1402 606/45 |
| 5,800,427 A | * | 9/1998 | Zamba ............... A61B 18/1402 606/39 |
| 5,800,449 A | * | 9/1998 | Wales ................ A61B 18/1447 606/172 |

(Continued)

FOREIGN PATENT DOCUMENTS

EP 0280798 A1 9/1988
WO 9940858 A1 8/1999

*Primary Examiner* — Linda C Dvorak
*Assistant Examiner* — Nils A Potter
(74) *Attorney, Agent, or Firm* — Zeman-Mullen & Ford, LLP (57) ABSTRACT

Electrosurgery blades including electrosurgery blade assemblies having argon beam capability. The electrosurgery blade includes a thin conductive member having a lead sharp cutting end and an opposite noon-cutting end and a non-conductive coating covering the thin conductive member such that at least a portion of the lead cutting end and at least a portion of the opposite non-cutting end of the thin conductive member remain exposed. An electrosurgery blade assembly having argon beam capability includes the previously described electrosurgery blade, a non-conductive tube member having a hollow tubular shaped opening positioned on top of the electrosurgery blade, and a conductive hollow tubular member contained within at least a portion of the non-conductive tube member.

15 Claims, 4 Drawing Sheets

(56) References Cited

U.S. PATENT DOCUMENTS

| | | | | |
|---|---|---|---|---|
| 6,053,929 | A * | 4/2000 | Cohn | A61B 17/3213 30/151 |
| 6,371,956 | B1 * | 4/2002 | Wilson | A61B 18/1445 606/49 |
| 2003/0130655 | A1 | 7/2003 | Woloszko et al. | |
| 2003/0181904 | A1 * | 9/2003 | Levine | A61B 18/1402 606/45 |
| 2006/0129145 | A1 * | 6/2006 | Woloszko | A61B 18/12 606/41 |
| 2006/0241588 | A1 * | 10/2006 | Heim | A61B 18/1402 606/48 |
| 2007/0142833 | A1 * | 6/2007 | Dycus | A61B 18/1445 606/51 |
| 2009/0118731 | A1 * | 5/2009 | Young | A61B 18/1477 606/48 |
| 2009/0171339 | A1 * | 7/2009 | Young | A61B 18/148 606/33 |
| 2012/0116267 | A1 * | 5/2012 | Kimball | A61B 18/04 601/2 |
| 2013/0331657 | A1 * | 12/2013 | Basson | A61B 90/30 600/249 |
| 2015/0327880 | A1 * | 11/2015 | Wasicek | A61B 17/22 606/115 |
| 2015/0359585 | A1 * | 12/2015 | Weber | A61B 18/1402 606/49 |
| 2017/0056054 | A1 * | 3/2017 | Dickerson | A61B 17/320068 |

* cited by examiner

MONOPOLAR ELECTROSURGERY BLADE AND ELECTROSURGERY BLADE ASSEMBLY

CROSS-REFERENCE TO RELATED APPLICATIONS

This application claims priority to provisional patent application having Ser. No. 62/467,558, filed Mar. 6, 2017 and provisional patent application having Ser. No. 62/576,207, filed Oct. 24, 2017, which are herein incorporated by reference in their entireties,

FIELD OF INVENTION

The present invention is generally directed to a monopolar electrosurgery blade for use in an electrosurgery pencil/handpiece. More particularly, the present invention relates to a monopolar electrosurgery blade which includes a thin conductive member having a lead sharp cutting end and an opposite non-cutting end, and a non-conductive coating covering most of the thin conductive member except that at least a portion of the lead cutting end of the thin conductive member and at least a portion of the opposite non-cutting end of the thin conductive member remain exposed. At least a portion of the top of the thin conductive member may also remain exposed and not covered by the non-conductive coating. The non-cutting end of the thin conductive member may comprise opposing prong members located opposite the lead cutting end and a conductive shaft having a first end and a second end where the first end of the conductive shaft is positioned between and in contact with the opposing prong members of the thin conductive member. The non-conductive coating covering the thin conductive member covers at least a portion of the conductive shaft while the opposing ends of the respective opposing prong members of the thin conductive member may also be covered or may remain exposed. The monopolar electrosurgery blade of the present invention is capable of cutting tissue with the sharp conductive cutting end of the blade without using RF energy, coagulating tissue and/or enhancing cutting of tissue by supplying low power to the sharp conductive cutting end of the blade, and simultaneously cutting and coagulating tissue by cutting tissue with the sharp conductive cutting end of the blade while applying low power to the sharp conductive cutting end of the blade.

The present invention is also directed to a monopolar electrosurgery blade assembly having argon beam capability which includes the previously described monopolar electrosurgery blade, a non-conductive tube member having a hollow tubular shaped opening positioned on top of the electrosurgery blade, and a conductive hollow tubular member contained within at least a portion of the non-conductive tube member through which an inert gas can be supplied. The conductive hollow tubular member may include a conductive projection extending from an end of the conductive hollow tubular member contained within the non-conductive tube member. Argon gas that is supplied through the conductive hollow tubular member and into the non-conductive tube member is ionized and directed by the conductive projection of the conductive hollow tubular member. In another embodiment, a portion of the thin conductive member of the electrosurgery blade may be exposed on the top of the electrosurgery blade and contained within the non-conductive tube member and a conductive projection may extend from the exposed portion of the conductive member that is contained within the non-conductive tube member. The monopolar electrosurgery blade assembly of the present invention is capable of 1) cutting tissue using the sharp cutting edge of the blade alone, 2) coagulating tissue using argon plasma alone, 3) simultaneously cutting and coagulating tissue by performing argon plasma assisted cutting using the sharp cutting edge of the blade to cut and the conductive tube contained within the non-conductive tube to introduce argon gas for argon plasma coagulation, and 4) coagulating tissue by performing argon plasma assisted coagulation using the conductive cutting edge of blade to coagulate tissue at low power and the conductive tube contained within the non-conductive tube to introduce argon gas for argon plasma coagulation.

BACKGROUND OF THE INVENTION

Typical electrosurgical pencil use an electrode blade which functions as an active electrode for use performing cutting and coagulation during electrosurgery and a return electrode usually comprising an adhesive for attachment to a patient's skin. When the electrosurgery pencil is activated, the RF energy circulates from the active electrode to the return electrode through the patient's body with the distance between the active and return electrodes being fairly significant. Electrosurgery uses a RF generator and handpiece with an electrode to provide high frequency, alternating radio frequency (RF) current input at various voltages depending on the function, namely coagulation vs. cutting. For cutting, heat generated from continuous RF high voltage conduction can create a vapor pocket which vaporizes and explodes a small section of tissue cells which results in an incision. Because of the heat generated, the lateral damage to the tissue is great and the possible necrosis of the tissue is high. For coagulation, voltage is usually lower than in cut mode and the slower heating process results in less heat. As a result, no vapor pocket is formed so the tissue for the most part remains intact but with cells and vessels destroyed and sealed at the point of contact.

Since surgical tools and devices currently available to surgeons require switching between cutting and coagulation nodes during the surgical procedure, there is a need for a surgical device or tool that enables a surgeon or user to utilize the best methods used for cutting and cessation of bleeding at the surgical site at the same time, or simultaneously, in addition to being able to use them separately. An electrosurgery blade having a sharp edge for cutting and RF for coagulation would meet this need. The monopolar electrosurgery blade of the present invention has a sharp cutting edge made of a hard conductive material, such as stainless steel, that can be used for precisely cutting tissue without the use of RF energy. However, RF energy can also be used with the monopolar electrosurgery blade of the present invention for coagulation. When low voltage is used to supply power to the monopolar electrosurgery blade of the present invention for coagulation, the sharp cutting edge of the monopolar electrosurgery blade can simultaneously be used for cutting without the need to provide higher voltage to carry out the cutting. Moreover, the low power used to employ the monopolar electrosurgery blade of the present invention for both cutting and coagulation substantially reduces the damage to the lateral tissue.

It is also common to use argon beam coagulators during electrosurgery, In argon beam coagulation (ABC), plasma is applied to tissue by a directed beam of ionized argon gas (plasma) which causes a uniform and shallow coagulation surface thereby stopping blood loss. In some instances, electrosurgery is often the best method for cutting and argon beam coagulation is often the best method for cessation of bleeding during surgery. Surgeons typically need to switch between argon beam coagulation and. electrosurgery modes depending on what is happening during the surgery and what they need to achieve at a particular point in the surgery such as making incisions in tissue by cutting, or stopping the bleeding at the surgical site.

Since surgical tools and devices currently available to surgeons require switching between cutting and argon beam coagulation during the surgical procedure, there is a need for a surgical device or tool that enables a surgeon or user to utilize the best methods used for cutting and cessation of bleeding at the surgical site at the same time, or simultaneously, in addition to being able to use them separately. An electrosurgery blade having a sharp edge for cutting and argon beam capability for capsulation would meet this need. There is also a need for an electrosurgical device that enables a user or surgeon to choose from a number of different separate or combined tissue cutting and coagulation methods since different methods may work best depending on the surgical procedure and circumstances that present themselves during surgery.

The electrosurgery blade assembly of the present invention is capable of coagulating a patient's tissue using argon plasma alone without contacting the patient's, tissue (i.e. non-contact argon beam coagulation). The electrosurgery blade assembly of the present invention is also capable of cutting a patient's tissue using the sharp conductive cutting edge of the blade alone without any use of RF energy and without any use of argon plasma. The electrosurgery blade assembly of the present invention can also enhance the cutting of a patient's tissue using the sharp conductive cutting edge of the blade by also supplying RE energy to the sharp conductive cutting edge of the blade. Moreover, the electrosurgery blade assembly of the present invention having a sharp conductive cutting edge and argon beam capability enables a user or surgeon to simultaneously perform cutting and coagulation without the need to switch between cutting and coagulation modes by performing argon plasma assisted cutting and coagulation. For example, the sharp conductive cutting, edge of the blade can be used without any RE energy for cutting while the conductive tube through which the argon gas is introduced, and which is contained within the non-conductive tube, is activated to provide ionized argon gas for argon plasma coagulation of tissue. In another example, low power may be applied to the conductive cutting edge of the blade to coagulate tissue or enhance cutting of tissue while the conductive tube through which the argon gas is introduced, and which is contained within the non-conductive tube, is activated to provide ionized argon gas for argon plasma coagulation of tissue.

Both the monopolar electrosurgery blade of the present invention and the monopolar electrosurgery blade assembly having argon beam capability of the present invention could be used with an electrosurgery handpiece/pencil with smoke evacuation capability or an electrosurgery handpiece/pencil without smoke evacuation capability. Both the monopolar electrosurgery blade of the present invention and the monopolar electrosurgery blade assembly having argon beam capability of the present invention enable the surgeon or user to increase both the efficiency and accuracy of the surgery by enabling the surgeon or user to perform different methods of cutting and coagulating tissue either separately or simultaneously. In instances where tissue cutting and coagulation are performed at the same time without switching between modes or methods, operating time is decreased and the lateral damage to the tissue is reduced or eliminated.

In addition, performing both tissue cutting and coagulation at the same time along with smoke evacuation will protect the surgeon and staff from inhaling smoke and particles. It will also enable the surgeon or user to more clearly view the surgical site to ensure accuracy during the procedure without the need to stop and switch modes in order to stop bleeding at the surgery site before being able to clearly see the surgical site.

SUMMARY OF THE INVENTION

The present invention is directed to a monopolar electrosurgery blade for use with an electrosurgery handpiece pencil with smoke evacuation, or an electrosurgery handpiece pencil without smoke evacuation, that includes a thin conductive member having a lead cutting end and an opposite. non-cutting end and a non-conductive coating covering the thin conductive member such that at least a portion of the lead cutting end of the thin conductive member and at least a portion of the opposite non-cutting end of the thin conductive member remain exposed, In addition, in one exemplary embodiment, at least a portion of the top of the thin conductive member may also remain exposed and not covered by the non-conductive coating. In another exemplary embodiment, the non-cutting end of the thin conductive member may comprise opposing prong members located opposite the lead cutting end and a conductive shaft having, a first end and a second end where the first end of the conductive shaft is positioned between and in contact with the opposing prong members of the thin conductive member where the no conductive coating, covering the thin conductive member also covers at least a portion of the conductive shaft. The opposing ends of the respective opposing prong members of the thin conductive member may also he covered by the non-conductive coating or may remain exposed. The width of the middle of the thin conductive member is less than the width of its cutting end and the width of each of its opposing prongs is less than its middle width.

The non-conductive coating may comprise an inorganic, non-metallic solid material, such as a ceramic, for example. The thin conductive member and conductive shaft may comprise one or more hard conductive materials such as, for example, stainless steel, titanium, and tungsten.

The leading cutting end of the electrosurgery blade may form any number of angles relative to a bottom of the electrosurgery blade including angles that are greater than ninety degrees. The thin conductive member may further include an opening therethrough located between the leading cutting end and the opposite non-cutting end to facilitate the construction of the monopolar electrosurgery blade and to enhance the strength and function of the monopolar electrosurgery blade. The opening is completely covered by the non-conductive coating. Further, the non-conductive coating may cover at least a portion of a top and bottom of the thin conductive member and the non-conductive coating may completely cover the first end of the conductive shaft.

The thin conductive member may comprise any number of thicknesses and in one exemplary embodiment, the thin conductive member may have a thickness between 0.2 mm and 0.8 mm. The thin conductive member may also comprise any number widths and lengths and in one exemplary embodiment the thin conductive member may have a width between 2 mm and to 6 mm, depending on where the width measurement is taken, and a length between 40 mm to 52 mm. Further, the thickness of the electrosurgery blade which includes the thin conductive member covered by the non-conductive coating member may comprise an number of thicknesses and in one exemplary embodiment the thickness of the electrosurgery blade which includes the thin conductive member covered by the non-conductive coating member may be between 2 mm to 6 mm. It will be understood by those skilled in the art that although these exemplary measurements may work well given the configuration and functional elements of the electrosurgery blade of the present invention, these measurements are merely exemplary measurements since the electrosurgery blade of the present invention may function quite well with elements having measurements outside of these exemplary ranges. Accordingly, these exemplary measurements are not intended to limit the scope of the present invention in any way.

The present invention is also directed to a monopolar electrosurgery blade assembly having argon beam capability whit h includes the previously described monopolar electrosurgery blade, a non-conductive tube member having a hollow tubular shaped opening and a slot which can be positioned over a portion of the electrosurgery blade, and a conductive hollow tubular member contained within at least a portion of the non-conductive tube through which an inert gas can be supplied. The conductive hollow tubular member may include a conductive projection extending from an end of the conductive hollow tubular member contained within the non-conductive tube member. Argon gas that is supplied through the conductive hollow tubular member and into the non-conductive tube member is ionized and directed by the conductive projection of the conductive hollow tubular member. In another embodiment, a portion of the thin conductive member of the electrosurgery blade may be exposed on the top of the electrosurgery blade and contained within the non-conductive tube member and a conductive projection may extend from the exposed portion of the conductive member that is contained within the non-conductive tube member. The exposed portion of the thin conductive member on the top of the electrosurgery blade is in contact with the conductive hollow tubular member contained within the non-conductive tube member and the conductive hollow tubular member may also include a slot for positioning the conductive hollow tubular member over a top of the electrosurgery blade. Like the non-conductive coating in the monopolar electrosurgery blade, the non-conductive tube member may comprise an inorganic, non-metallic solid material, such as a ceramic, for example. The conductive hollow tubular member may comprise a hard metal such as, for example, stainless steel, titanium, and tungsten.

BRIEF DESCRIPTION OF THE DRAWINGS

The subject invention will hereinafter be described in conjunction with the appended drawing figures, wherein like numerals denote like elements.

DETAILED DESCRIPTION or EXEMPLARY EMBODIMENTS

The exemplary embodiments of the, monopolar electrosurgery blade and monopolar electrosurgery blade assembly having argon beam capability of the present invention enable the surgeon or user to increase both the efficiency and accuracy of the surgery by enabling the surgeon or user to perform different methods of cutting and coagulating tissue either separately or simultaneously. In instances where tissue cutting and coagulation are performed at the same time without switching between modes or methods, operating time is decreased and the lateral damage to the tissue is reduced or eliminated. Exemplary embodiments of the monopolar electrosurgery blade and the monopolar electrosurgery blade assembly of the present invention include an electrosurgery blade that has a thin conductive member having a lead cutting end and an opposite non-cutting end and a non-conductive coating covering the thin conductive member so that a portion of the lead cutting end of the thin conductive member and a portion of the opposite non-cutting end of the thin conductive member remain exposed. The thin conductive member may include an opening through it which is located between the lead cutting end and the opposite non-cutting cud where the opening is completely covered by the non-conductive coating. This configuration facilitates construction of the electrosurgery blade while enhancing the strength and functioning of the blade. In addition, in one exemplary embodiment, at least a portion of the top of the thin conductive member may also remain exposed and not covered by the non-conductive coating. In another exemplary embodiment, the non-cutting end of the thin conductive member may include opposing prong members located opposite the lead cutting end and a conductive shaft having a first end and a second end where the first end of the conductive shaft is positioned between and in contact with the opposing prong members of the thin conductive member where the non-conductive coating covering the thin conductive member also covers at least a portion of the conductive shaft.

The electrosurgery blade assembly having argon beam capability includes the monopolar electrosurgery blade described above, a non-conductive tube member having a hollow tubular shaped opening and a slot which can be positioned over a portion of the electrosurgery blade, and a conductive hollow tubular member, through which an inert gas can be supplied, contained within at least a portion of the non-conductive tube. The electrosurgery blade assembly of the present invention is capable of 1) cutting tissue using the sharp cutting edge of the blade alone, 2) coagulating tissue using argon plasma alone, 3) simultaneously cutting and coagulating tissue by performing argon plasma assisted cutting using the sharp cutting edge of the blade to cut and the conductive tube contained within the non-conductive tube to introduce argon gas for argon plasma coagulation, and 4) coagulating tissue by performing argon plasma assisted coagulation using the conductive cutting edge of the blade to coagulate tissue at low power and the conductive tube contained within the non-conductive tube to introduce argon gas for argon plasma coagulation.

The identity of the elements/features that relate to the numbers shown in the drawing figures are as follows:
- 10 electrosurgery
- 12 thin conductive member
- 13 opposing planar sides
- 14 top (of thin conductive member)
- 16 bottom (of thin conductive member)
- 18 lead sharp cutting end (of thin conductive member)
- 19 exposed area (of thin conductive member extending along top of blade from lead sharp cutting end)
- 20 opposite non-cutting end (of thin conductive member)
- 22 opposing prong members (of opposite non-cutting end)
- 24 opening (in thin conductive member)
- 30 conductive shaft
- 32 first end (of conductive shaft)
- 34 second end (of conductive shall)
- 40 non-conductive coating
- 50 electrosurgery blade assembly with argon beam capability
- 52 thin conductive member
- 54 top (of thin conductive member)
- 56 bottom (of thin conductive member)
- 58 lead cutting end (of thin conductive member)
- 70 conductive shaft
- 72 first end (of conductive shaft)
- 74 second end (of conductive shaft)
- 80 non-conductive coating
- 90 non-conductive tube member
- 92 hollow tubular shaped opening (in non-conductive tube member)
- 93 slot (in non-conductive tube member)
- 94 conductive hollow tubular member
- 96 conductive projection (of hollow conductive tubular member)
- 150 electrosurgery blade assembly with argon beam capability
- 152 thin conductive member
- 154 top (of thin conductive member)
- 156 bottom (of thin conductive member)
- 158 lead cutting end (of thin conductive member)
- 159 exposed area (of this conductive member extending along top of blade from lead sharp cutting end)
- 170 conductive shaft
- 180 non-conductive coating
- 190 non-conductive tube member
- 192 hollow tubular shaped opening (in non-conductive tube member)
- 193 slot (in non-conductive tube member)
- 194 conductive hollow tubular member
- 195 conductive projection (extending from top of thin conductive member contained within non-conductive tube member)

Figure 1:
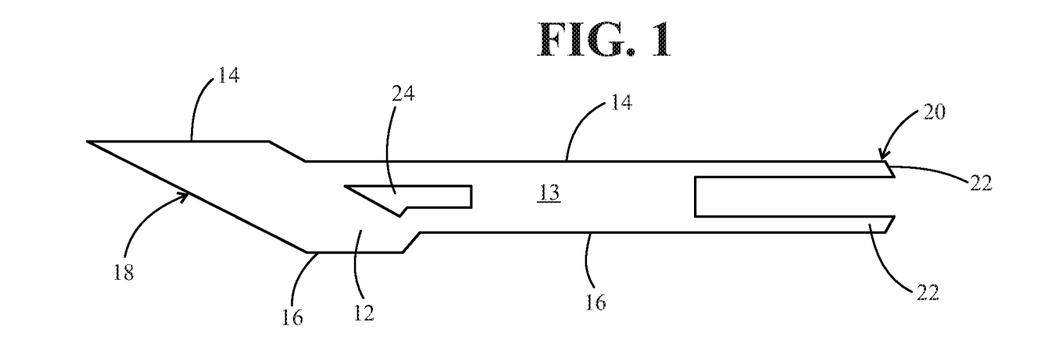
FIG. 1 is a side view of an exemplary embodiment of the thin conductive member of the monopolar electrosurgery blade of the present invention.

A side view of an exemplary embodiment of the thin conductive member 12 of the monopolar electrosurgery blade 10 of the present invention is shown in FIG. 1. Thin conductive member 12 has opposing planar sides 13, a top 14, a bottom 16, a lead sharp cutting end 18 and an opposite non-cutting end 20. The opposite non-cutting end 20 may include two opposing prong members 22. The thin conductive member 12 may also include an opening 24 located between the lead sharp cutting end 18 and the opposite non-cutting end 20.

Figure 2:
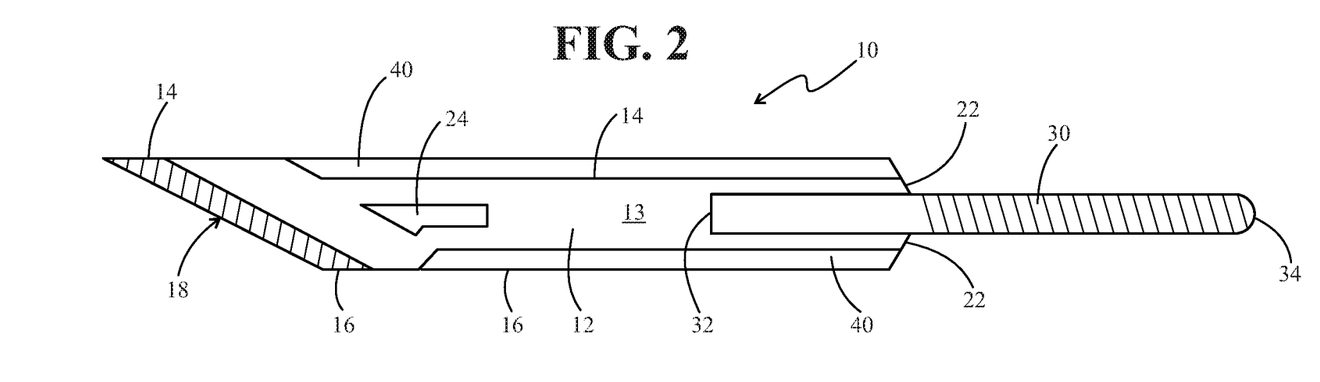
FIG. 2 is a side view of an exemplary embodiment of the monopolar electrosurgery blade of the present invention which shows the internal components of the blade including the thin conductive member shown in FIG. 1 and a conductive shaft, and which further identifies the exposed sharp conductive cutting end of the electrosurgery blade by showing it with slanted hash marks (note that all of the thin conductive member 12 and the conductive shaft 30 are conductive even though only those portions nut covered by non-conductive coating 40 are shown with slanted hash marks in the drawing)

FIG. 2 is a side view of an exemplary embodiment of the monopolar electrosurgery blade 10 of the present invention which shows the internal components of the blade including the thin conductive member 12 shown in FIG. 1 and a conductive shaft 30. In addition to the thin conductive member 12, the monopolar electrosurgery blade 10 further includes a non-conductive coating 40 which covers the thin conductive member 12 except for a portion of the lead cutting edge 18 which remains exposed as shown by the slanted hash marks. Accordingly, at least a portion of the top 14 of the thin conductive member 12 and a portion of the bottom 16 of thin conductive member 12 remain exposed. The electrosurgery blade 10 may further include a conductive shaft 30 having a first end 32 and a second end 34 where the first end 32 is positioned between, and in contact with, the opposing prong members 22 of the thin conductive member 12. It should be noted that all of the thin conductive member 12 and the conductive shaft 30 shown in FIG. 2 are conductive even though only those portions not covered by non-conductive coating 40 are shown with slanted hash marks. Non-conductive coating 40 covers the opening 24 in the thin conductive member 12 and the first end 32 of the conductive shaft 30. The opening 24 within the thin conductive member 12 facilitates the construction of the electrosurgery blade 10 while enhancing the strength and function of the electrosurgery blade. The ends of opposing prong members 22 may also he covered by non-conductive coating 40 or they may remain exposed.

Figures 3, 4, 6:
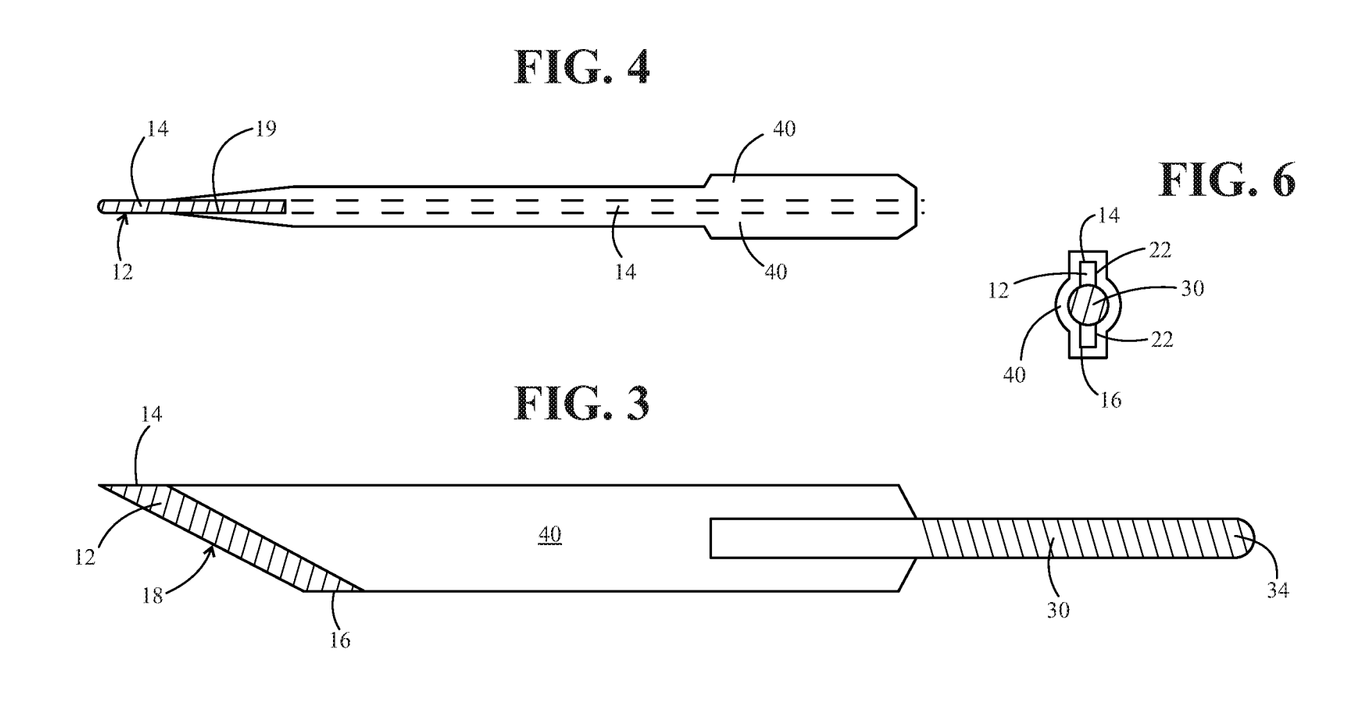
FIG. 3 is an external side view showing the exemplary embodiment of the electrosurgery blade of the present invention shown in FIG. 2.
FIG. 4 is a top view of the exemplary embodiment of the electrosurgery blade of the present invention shown in FIGS. 2-3 within the conductive shaft and with the portion of the thin conductive member contained within the non-conductive coating shown in phantom.
FIG. 6 is an end view of the exemplary embodiment of the electrosurgery blade of the present invention shown in FIGS. 2-3 with the conductive shalt shown with slanted hash marks.

FIG. 3 is an external side view showing the exemplary embodiment of the electrosurgery blade 10 of the present invention shown in FIG. 2. As seen in FIG. 3, non-conductive coating 40 covers almost all of thin conductive member 12 except for the leading cutting edge 18 and it also covers the first end 32 of conductive shaft 30 which is positioned between and in contact with opposing prong members 22 of thin conductive member 12. The second end 34 of conductive shaft 30 remains exposed for electrical connection within an electrosurgery pencil (not shown) which utilizes the electrosurgery blade 10 of the present invention. Some of conductive shaft 30 that extends beyond the ends of opposing prong members 22 of the thin conductive member 12 may also be covered with non-conductive coating 40 or an insulating material as long as at least a part of the second end 34 of conductive shaft 30 remains exposed for electrical connection within an electrosurgery pencil. In addition, the ends of opposing prong members 22 of thin conductive member 12 may remain exposed as shown in FIG. 6 or may also be covered with non-conductive coating 40. FIG. 6 is, an end view of the exemplary embodiment of the electrosurgery blade 10 of the present invention shown in FIGS. 2-3 with the conductive shaft 30 shown with slanted hash marks.

Figure 5:
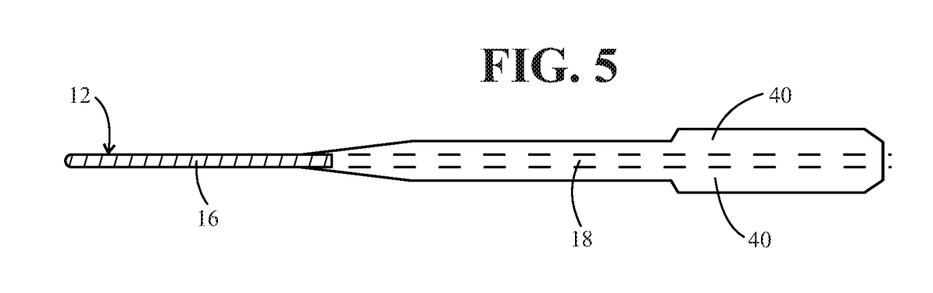
FIG. 5 is a bottom view of the exemplary embodiment of the electrosurgery blade of the present invention shown in FIGS. 2-3 without the conductive shaft and with the portion of the thin conductive member contained within the non-conductive coating shown in phantom.

FIG. 4 is a top view of the exemplary embodiment of the electrosurgery blade 10 of the present invention shown in FIGS. 2-3 without the conductive shaft and with the portion of the thin conductive member contained within the non-conductive coating shown in phantom and FIG. 5 is a bottom view of the exemplary embodiment of the electrosurgery blade of the present invention shown in FIGS. 2-3 without the conductive shaft and with the portion of the thin conductive member contained within the non-conductive coating shown in phantom. As can he seen in FIG. 4, one exemplary embodiment of the electrosurgery blade 10 of the present invention may include an exposed area 19 of the thin conductive member 12 located at a top of the electrosurgery blade 10 and extending further along the top of the electrosurgery blade 10 from the portion of the thin conductive member exposed at the lead sharp cutting end 18 of the thin conductive member 12.

Figure 7:
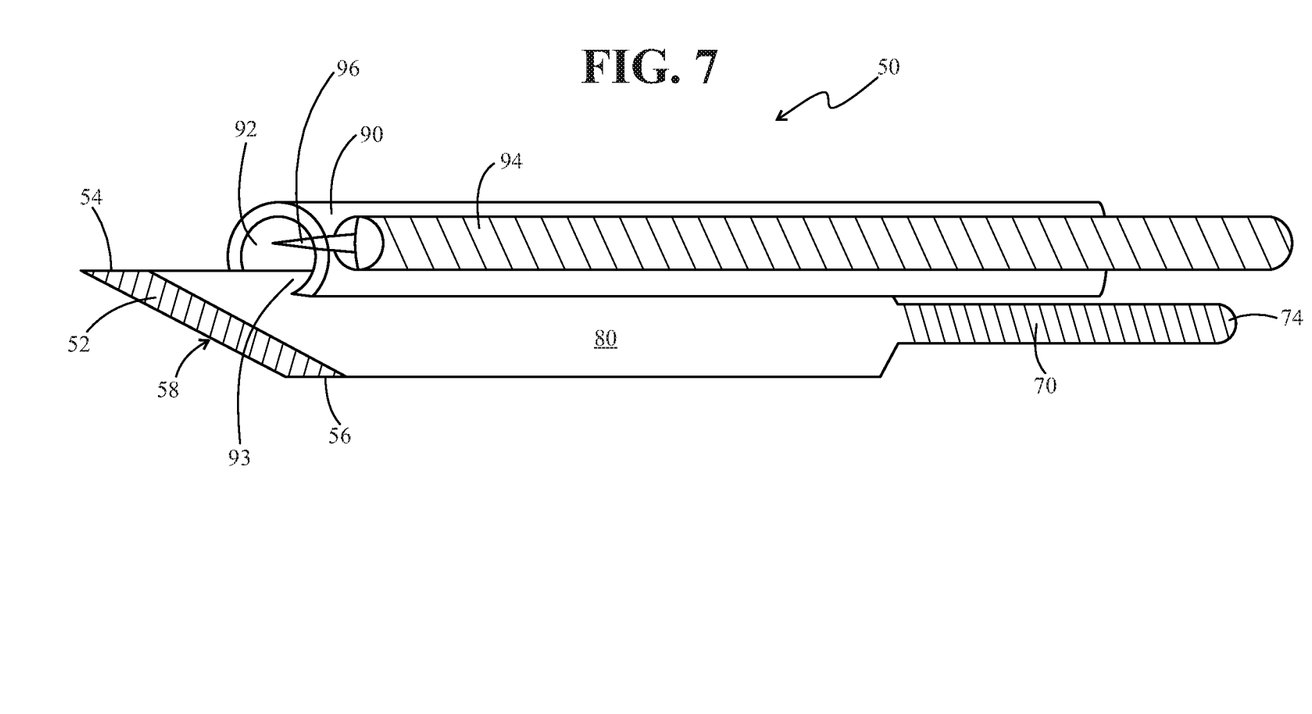
FIG. 7 is an external side view showing internal components of an exemplary embodiment of the monopolar electrosurgery blade assembly with argon, beam capability of the present invention.

An external side view showing internal components of exemplary embodiment of the electrosurgery blade assembly 50 with argon beam capability of the present invention is shown in FIG. 7. Electrosurgery blade assembly 50 includes the same electrosurgery blade previously described with reference to FIGS. 1-6, namely an electrosurgery blade having a thin conductive member 52, a non-conductive coating 80 which covers the thin conductive member 52 except for a portion of the lead cutting edge 58 which remains exposed as shown by the slanted hash marks. Accordingly, at least a portion of the top 54 of the thin conductive member 52 and a portion of the bottom 56 of thin conductive member 52 remain exposed. The electrosurgery blade may further include a conductive shaft 70 having a first end positioned between, and in contact with, opposing prong members of the thin conductive member 52 as shown in FIG. 2. Non-conductive coating 80 covers an opening in the thin conductive member 52 and the first end of the conductive shaft 70. The electrosurgery blade assembly 50 further includes a non-conductive tube member 90 having a hollow tubular shaped opening 92 and a slot 93 for positioning the non-conductive tube member 90 over a top of the electrosurgery blade and a conductive hollow tubular member 94 contained within at least a portion of the non-conductive tube member 90. Conductive hollow tubular member 94 may include a conductive projection 96 extending from an end of the conductive hollow tubular member 94 that is contained within the non-conductive tube member 90. Argon gas that is supplied through the conductive hollow tubular member 94 and into the non-conductive tube member 90 is ionized and directed by the conductive projection 96 of the conductive hollow tubular member 94. Active conductive components of the electrosurgery blade assembly 50 of the present invention are represented by having slanted hash marks.

Figure 8:
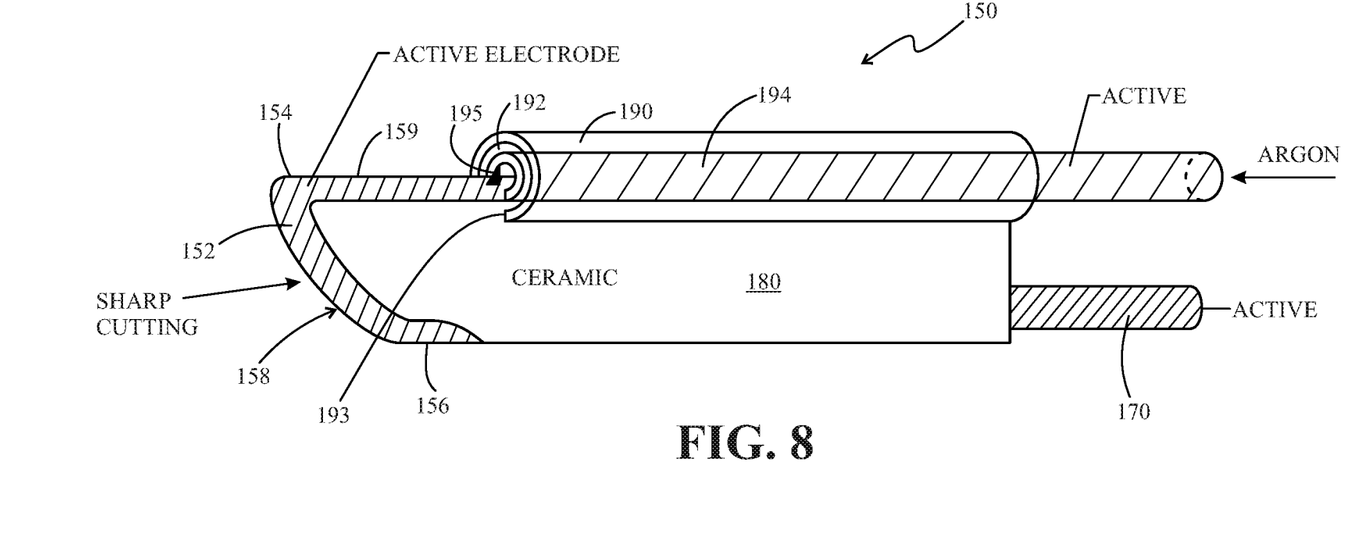
FIG. 8 is an external side view showing internal components of another exemplary embodiment of the monopolar electrosurgery blade assembly with argon beam capability of the present invention.

FIG. 8 is an external side view showing internal components of another exemplary embodiment of the monopolar electrosurgery blade assembly 150 with argon beam capability of the present invention. Like electrosurgery blade assembly 50 shown in FIG. 7, electrosurgery blade assembly 150 includes the same electrosurgery blade previously described with reference to FIGS. 1-6, namely an electrosurgery blade having a thin conductive member 152, a non-conductive coating 180 which covers the thin conductive member 152 except for a portion of the lead cutting edge 158 which remains exposed as shown by the slanted hash marks. Accordingly, at least a portion of the top 154 of the thin conductive member 152 and a portion of the bottom 156 of thin conductive member 152 remain exposed. Further, as shown in this exemplary embodiment, there is an exposed area 159 of the thin conductive member 152 located at a top of the electrosurgery blade and extending further along the top of the electrosurgery blade from the portion of the thin conductive member 152 exposed at the lead sharp cutting end 158 of the thin conductive member 152. The electrosurgery blade may further include a conductive shall 170 having a first end positioned between, and in contact with, opposing prong members of the thin conductive member 152 as shown in FIG. 2. Non-conductive coating 180 covers an opening in the thin conductive member 152 and the first end of the conductive shaft 170. The electrosurgery blade assembly 150 further includes a non-conductive tube member 190 having a hollow tubular shaped opening 192 and a slot 193 for positioning the non-conductive tube member 190 over a top of the electrosurgery blade and a conductive hollow tubular member 194 contained within at least a portion of the non-conductive tube member 190. A conductive projection 195 may extend from the exposed area 159 of the thin conductive member on the top of the electrosurgery blade that is contained within the non-conductive tube member 190. The exposed area 159 of the thin conductive member on the top of the electrosurgery blade is in contact with, or located very near, the conductive hollow tubular member 194 contained within the non-conductive tube member 190 and the conductive hollow tubular member 194 may also include a slot for positioning the conductive hollow tubular member 194 over a top of the electrosurgery blade. Argon gas that is supplied through the conductive hollow tubular member 194 and into the non-conductive rube member 190 is ionized and directed by the conductive projection 195 extending from the exposed area 159 of the thin conductive member of the electrosurgery blade. Alternatively, the conductive hollow tubular member 190 may include a conductive projection, like that previously described with reference to FIG. 7, that directs ionized gas. Active conductive components of the electrosurgery blade assembly 150 of the present invention are represented by having slanted hash marks.

The exemplary embodiments of the monopolar electrosurgery blade assembly of the present invention can perform argon plasma coagulation and argon plasma assisted coagulation. More specifically, the exemplary embodiments of the electrosurgery blade assembly of the present invention are capable of 1) cutting tissue using the sharp cutting edge of the blade alone, 2) coagulating tissue using argon plasma alone, 3) simultaneously cutting and coagulating tissue by performing argon plasma assisted cutting using the sharp cutting edge of the blade to cut and the conductive tube contained within the non-conductive tube to introduce argon gas for argon plasma coagulation, and 4) coagulating tissue by performing argon plasma assisted coagulation using the conductive cutting edge of the blade to coagulate tissue at low power and the conductive tube contained within the non-conductive tube to introduce argon gas for argon plasma coagulation.

The non-conductive coating of the electrosurgery blade of the present invention may comprise an inorganic, non-metallic solid material, such as a ceramic, for example. The thin conductive member and conductive shaft of the electrosurgery blade of the present invention may comprise one or more hard conductive materials such as, for example, stainless steel, titanium, and tungsten. Like the non-conductive coating in the electrosurgery blade, the non-conductive tube member of the electrosurgery blade assembly of the present invention may comprise an inorganic, non-metallic solid material, such as a ceramic, for example. The conductive hollow tubular member of the electrosurgery blade assembly may comprise a hard metal such as, for example, stainless, titanium, and tungsten.

The description of exemplary embodiments of the invention herein shows various exemplary embodiments of the invention. These exemplary embodiments and modes are described in sufficient detail to enable those skilled in the art to practice the invention and are not intended to limit the scope, applicability, or configuration of the invention in any way. Rather, the following disclosure is intended to teach both the implementation of the exemplary embodiments and modes and any equivalent modes or embodiments that are known or obvious to those reasonably skilled in the art. Additionally, all included examples are non-limiting illustrations of the exemplary embodiments and modes, which similarly avail themselves to any equivalent modes or embodiments that are known or obvious to those reasonably skilled in the art.

Other combinations and/or modifications of structures, arrangements, applications, proportions, elements, materials, or components used in the practice of the instant invention, in addition to those not specifically recited, can be varied or otherwise particularly adapted to specific environments, manufacturing specifications, design parameters, or other operating requirements without departing from the scope of the instant invention and are intended to be included in this disclosure.

Unless specifically noted, it is the Applicant's intent that the words and phrases in the specification and the claims be given the commonly accepted generic meaning or an ordinary and accustomed meaning used by those of ordinary skill in the applicable arts. In the instance where these meanings differ, the words and phrases in the specification and the claims should be given the broadest possible, generic meaning. If any other special meaning is intended for any word or phrase, the specification will clearly state and define the special meaning.

The following claims are included as exemplary claims only and are not intended to define or limit the scope of patentable subject matter contained within the provisional patent application.

The invention claimed is:

1. An electrosurgery blade assembly comprising:
   an electrosurgery blade comprising:
      a thin conductive member having opposing planar sides, a lead sharp cutting end, an opposite non-cutting end, and a planar horizontal opening therethrough located between the lead sharp cutting end and the opposite non-cutting end wherein a middle width of the thin conductive member and a width of the non-cutting end of the thin conductive member are both less than a largest width of the lead sharp cutting end of the thin conductive member; and
      a non-conductive coating covering both opposing planar sides of the thin conductive member and its planar horizontal opening such that at least a portion of the lead sharp cutting end and at least a portion of the opposite non-cutting end of the thin conductive member remain exposed;
   a non-conductive tube member having a hollow tubular shaped opening contained therein positioned on a top of said electrosurgery blade such that it is in physical contact with the electrosurgery blade; and
   a conductive hollow tubular member contained within at least a portion of the non-conductive tube member.

2. The electrosurgery blade of claim 1 wherein the non-conductive coating covers a top and bottom of the thin conductive member while still leaving at least a portion of the top and bottom of the thin conductive member exposed.

3. The electrosurgery blade of claim 1 wherein the opposite non-cutting end comprises opposing prong members.

4. The electrosurgery blade of claim 3 further comprising a conductive shaft having a first end and a second end wherein the first end is positioned between and in contact with the opposing prong members of the opposite non-cutting end of the thin conductive member.

5. The electrosurgery blade of claim 4 wherein the non-conductive coating completely covers the first end of the conductive shaft.

6. The electrosurgery blade of claim 4 wherein the conductive shaft comprises a hard metal.

7. The electrosurgery blade of claim 1 wherein a middle width of the thin conductive member is less than a width of the thin conductive member located near the lead sharp cutting end of the thin conductive member.

8. The electrosurgery blade assembly of claim 1 further comprising a conductive projection extending from an end of the conductive hollow tubular member.

9. The electrosurgery blade assembly of claim 1 wherein at least a portion of the thin conductive member is exposed on a top of the electrosurgery blade and contained within the non-conductive tube member.

10. The electrosurgery blade assembly of claim 9 further comprising a conductive projection extending from the portion of the thin conductive member that is exposed on the top of the elearosurgery blade and contained within the non-conductive tube member.

11. The electrosurgery blade assembly of claim 1 wherein the non-conductive tube member comprises a ceramic.

12. The electrosurgery blade assembly of claim 1 wherein the conductive hollow tubular member comprises a hard metal.

13. The electrosurgery blade assembly of claim 1 wherein the non-conductive coating of the electrosurgery blade comprises a ceramic.

14. The electrosurgery blade assembly of claim 1 wherein the thin conductive member of the electrosurgery blade comprises a hard metal.

15. An electrosurgery blade assembly comprising:
   an electrosurgery blade comprising:
      a thin conductive planar member having opposing planar sides, an angled sharp cutting end, and an opposite non-cutting end terminating in opposing prongs wherein a middle width of the thin conductive planar member and a width of the opposite non-cutting end of the thin conductive planar member immediately preceding the opposing prongs are both the same and less than a largest width of the angled sharp cutting end of the thin conductive planar member; and
      a non-conductive coating covering the thin conductive member such that at least a portion of the angled sharp cutting end and at least a portion of the opposite non-cutting end of the thin conductive member remain exposed;
   a non-conductive tube member having a hollow tubular shaped opening contained therein positioned on a top of said electrosurgery blade such that it is in physical contact with the electrosurgery blade; and a conductive hollow tubular member contained within at least a. portion of the non-conductive tube member.

* * * * *